United States Patent [19]

Kowalsky et al.

[11] 4,348,379

[45] Sep. 7, 1982

[54] DIETETIC COMPOSITION FOR NATURAL DIGESTION REGULATION

[76] Inventors: Horst Kowalsky, Marzellenstrasse 1, Cologne 1, Fed. Rep. of Germany, 5000; Horst Scheer, Poststrasse 17, Bad Neuenahr, Fed. Rep. of Germany, 5483

[21] Appl. No.: 146,495

[22] Filed: May 5, 1980

[30] Foreign Application Priority Data

May 15, 1979 [DE] Fed. Rep. of Germany ....... 2919449

[51] Int. Cl.³ .................... A61K 9/34; A61K 35/78; A21D 10/00
[52] U.S. Cl. ........................... 424/34; 424/16; 424/195; 426/549; 426/804; 426/810
[58] Field of Search ............ 426/549, 804, 810; 424/195, 16, 34

[56] References Cited

U.S. PATENT DOCUMENTS 2,253,800  8/1941  Myers et al. ..................... 424/34
3,431,112  3/1969  Durst ................................. 426/810

FOREIGN PATENT DOCUMENTS 2626734  12/1977  Fed. Rep. of Germany ...... 426/804
396594  8/1933  United Kingdom ................ 424/195

OTHER PUBLICATIONS

Steinmetz, Codex Vegetabilis, 1957, items 661 and 863.

*Primary Examiner*—Donald B. Moyer
*Attorney, Agent, or Firm*—Hammond & Littell, Weissenberger & Muserlian

[57] ABSTRACT

A dietetic composition for natural digestion regulation, consisting of 50 to 150 parts by weight of whole fleawort seeds (*Semen psyllii totum*), 50 to 150 parts by weight of whole linseed, 50 to 150 parts by weight of wheat bran, 50 to 150 parts by weight of lactose, an amount of a binding agent based on natural rubber sufficient for binding these dry constituents, and optionally a flavor corrective and/or a food color.

4 Claims, No Drawings

DIETETIC COMPOSITION FOR NATURAL DIGESTION REGULATION

This invention relates to a novel dietetic composition for regulation of the natural digestion.

BACKGROUND OF THE INVENTION

Present-day habits of nutrition are characterized by an increasing consumption of purified natural products with a high calorie content, which are mostly easily digestible but contain hardly any roughage. Especially starch products and sugar, frequently combined in sweet baked articles, besides providing too copious a supply of fat, contribute to the fact that a large proportion of the population is subject not only to overweight and at the same time a disturbed digestion, but often also to genuine metabolic diseases with their subsequent phenomena. In innumerable cases the lack of roughage means that the passage of the ingested food through the intestine is controllable only by means of mostly chemical purgatives, whereby in almost all cases after a generally short period of habituation it is necessary to take ever stronger agents which frequently disable rather than stimulate the natural movements of the intestine and remove from the body not only considerable quantities of liquid, but also vital trace elements, vitamins and salts. The intestinal sluggishness caused by a lack of roughage in the food leads frequently to an excessively long residence time of this food in the intestine, so that also undesirable decomposition products can be absorbed by the body, which then lead, in turn, to the onset of diseases.

Attempts have been made for a long time to counteract the lack of roughage in modern nutrition by providing additional natural roughage in the form of wheat bran and other fibrous parts of cereals which, on the one hand, inhibit the feeling of hunger and, on the other hand, attempt, by being added to the normal diet, to compensate the lack of roughage in said diet. Unfortunately, the impairment of the customary flavor of the food after the addition of such roughage, or the separate ingestion thereof before a meal leads to the fact that, even after a short time, the simultaneous or separate ingestion of the roughage is abandoned despite favorable accompanying phenomena in respect of stool regulation and that, in its stead, purgatives are adopted again, not only to counter the excess of supplied calories, but above all to prevent constipation already chronic today. There has therefore been a genuine long-felt need to make available a composition for natural digestion regulation which, on the one hand, does not have the known disadvantages of conventional, particularly chemical purgatives, such as deprivation of liquids, vitamins, salts and minerals, and, on the other hand, can be supplied to the body separately from the absorption of food, that is, without impairing the flavor and consistency of this food, and which regulates digestion again so naturally that even chronic constipation is eliminated without purgatives and especially without their generally eight-hour rhythm felt to be unpleasant by most patients.

DESCRIPTION OF THE INVENTION

We have discovered that the above-indicated problems are overcome by a dietetic composition which consists of the whole ripe dried seed of Plantago psyllium Linne and Plantago arenaria Waldstein and Kitaibel, known as fleawort seed or Semen psyllii, whole linseed, bran, lactose and a quantity, sufficient for binding these dry constituents, of a binding agent based on natural rubber, and which further optionally contains flavor correctives and food coloring substances and is molded as desired.

Although the activity of linseed and wheat bran as roughage has been known for a long time, and also knowing of the activity both of linseed and of fleawort seed as digestion regulators, it is nevertheless all the more surprising that due to the combination of the constituents of the composition according to the present invention, natural digestion regulation becomes possible without the unpleasant accompanying phenomena of a purgative being observed.

The dietetic composition of the present invention for natural digestion regulation consists of 50 to 150 parts by weight of Semen psyllii totum (fleawort seed), 50 to 150 parts by weight of Semen Lini totum (linseed), 50 to 150 parts by weight of wheat bran and 50 to 150 parts by weight of lactose, as well as of a quantity, sufficient for binding these dry constituents, of a binding agent based on natural rubber and optionally of flavor correctives and/or food coloring substances. A composition containing 80 to 120 parts by weight of the above-mentioned dry constituents and, relative to the mixture of these constituents, 2% to 5% by weight, preferably 2.5% by weight, of a binding agent based on natural rubber has proved especially successful. Gum arabic can preferably be used as the binding agent based on natural rubber, namely 5 to 25 parts by weight of gum arabic. Honey, sugar substitutes and/or sweetening agents, as well as suitable officially approved coloring substances can be used in the composition of the present invention for flavor improvement.

A composition according to the invention which contains fleawort seed, linseed, wheat bran and lactose in approximately equal quantities has proved preeminently suitable. In this case, very small quantities of gum arabic are sufficient as binding agent component, namely 2.5% by weight relative to the mixture consisting of fleawort seed, linseed, wheat bran and lactose.

Honey, sugar substitutes, especially fruit sugar, as well as synthetic sweetening agents and other flavor correctives, among other things also small quantities of cocoa powder, can be used in quantities which impart a pleasant flavor to the composition. For example, honey can be employed in an amount of 10% by weight relative to the above-mentioned dry mixture.

The preparation of the dietetic composition for natural digestion regulation according to the present invention can be effected appropriately by first mixing the binding agent with water and allowing it to stand until complete dissolution or swelling. The further constituents of the composition are then added with thorough mixing, whereupon the mixture is optionally left as it is until it has assumed a consistency suitable for molding. The molding can then be effected in a molding maching in a way known to a person skilled in the art, for example, with the formation of moldings similar to baked articles, such as round, angular or randomly shaped cakes or biscuits, which are subsequently dried at product temperatures up to 60° C., preferably up to 50° C., in a drying oven or on a belt drier.

The invention is illustrated by means of the following example:

EXAMPLE 10 gm of gum arabic were admixed with 200 ml of water and left to stand until complete swelling. After addition of 40 gm of honey or a corresponding quantity of another sweetening agent, for example sodium cyclamate, a previously prepared dry mixture of 100 gm each of whole fleawort seed, whole linseed, wheat bran and lactose was added and thoroughly admixed, whereupon the total mixture was allowed to stand at room temperature for 30 to 45 minutes. With the aid of a conventional molding machine the mixture was compressed into about 40 biscuits and dried on a belt drier so that the temperature in the product did not substantially exceed 50° C.

Two of these biscuits, chewed well and swallowed with any desired liquid at any time, preferably in the afternoon, make it superfluous, even after a very short time, for a patient with chronic constipation to ingest any purgatives, and they lead to a natural digestion regulation without undesirable deprivation of liquid, minerals and salts.

We claim:

1. A dietetic composition for natural digestion regulation, consisting of 50 150 parts by weight of whole fleawort seeds, 50 to 150 parts by weight of whole linseed, 50 to 150 parts by weight of wheat bran, 50 to 150 parts by weight of lactose, an amount of a gum sufficient for binding these dry constituents, and optionally a flavor corrective and/or a food color.

2. A composition of claim 1, consisting of 80 to 120 parts by weight of the dry constituents mentioned in claim 1 and, relative to the mixture of these constituents, 2 to 5% by weight, preferably 2.5% by weight, of a gum.

3. A composition of claim 1, where said gum is gum arabic.

4. A composition of claim 1 which contains honey, a sugar substitute and/or a sweetening agent as the flavor corrective.

* * * * *